United States Patent [19]

Blank et al.

[11] Patent Number: 5,206,427
[45] Date of Patent: Apr. 27, 1993

[54] PROCESS FOR THE PREPARATION OF AROMATIC (DI)CHLOROSULPHONIC ACIDS AND (DI)BROMOSULPHONIC ACIDS

[75] Inventors: Heinz U. Blank, Odenthal; Uwe Heinz, Cologne, both of Fed. Rep. of Germany

[73] Assignee: Bayer Aktiengesellschaft, Leverkusen, Fed. Rep. of Germany

[21] Appl. No.: 741,985

[22] Filed: Aug. 6, 1991

Related U.S. Application Data

[63] Continuation of Ser. No. 577,378, Sep. 4, 1990, abandoned.

[30] Foreign Application Priority Data

Sep. 16, 1989 [DE] Fed. Rep. of Germany ....... 3930994

[51] Int. Cl.$^5$ .................. C07C 303/00; C07C 307/00; C07C 309/00
[52] U.S. Cl. ........................ 562/83; 562/59; 562/69; 562/73; 562/75; 562/76; 562/78
[58] Field of Search .................... 562/83, 59, 69, 73, 562/75, 76, 78

[56] References Cited

U.S. PATENT DOCUMENTS 4,131,619 12/1978 Pews .

FOREIGN PATENT DOCUMENTS 0057889  8/1982  European Pat. Off. .
 312959  6/1919  Fed. Rep. of Germany .
 491220  2/1930  Fed. Rep. of Germany .
2297836  1/1976  France .
1-258656 10/1989 Japan ..................................... 562/83
1017976  1/1966  United Kingdom ................... 563/83

OTHER PUBLICATIONS

Bernhard Prager et al.; "Beilsteins Handbuch Der Organischen Chemie" pp. 56–57; 1928.

Primary Examiner—Alan Siegel

[57] ABSTRACT

Aromatic (di)chlorosulphonic acids and (di)bromosulphonic acids can be prepared by reacting aromatic sulphonic acids with chlorine or bromine respectively, the reaction advantageously being carried out in the melt of the aromatic sulphonic acids.

10 Claims, No Drawings

PROCESS FOR THE PREPARATION OF AROMATIC (DI)CHLOROSULPHONIC ACIDS AND (DI)BROMOSULPHONIC ACIDS

This application is a continuation of application Ser. No. 577,378, filed Sep. 4, 1990 now abandoned.

BACKGROUND OF THE INVENTION

The present invention relates to a process for the preparation of aromatic (di)chlorosulphonic acids and (di)bromosulphonic acids. Such aromatic sulphonic acids which are monohalogenated or dihalogenated are intermediates which can be used for a large number of purposes, for example for the preparation of colorants or plant protection agents.

According to previous processes, aromatic sulphonic acids can be chlorinated for example in such a way that the sulphonic acid is brought into contact with chlorine either in a polar solvent such as water or sulphuric acid or in an inert solvent, with the simultaneous presence of a catalyst. The sulphonation of the basic aromatic compound and the chlorination are frequently carried out one after the other in the same reaction batch. Examples of the first-mentioned embodiment are given in EP 57,889 or DE-OS (German Published Specification) 2,501,899. An example which may be mentioned of the second embodiment mentioned is U.S. Pat. No. 4,131,619. Both embodiments mentioned correspond to the ionic mechanism of this chlorination. Both variants have the disadvantage that large amounts of contaminated solvents are obtained which must either be eliminated or worked up for recycling; if a catalyst is simultaneously used, the latter is also to be treated.

There was therefore a demand to have available a process which permits chlorination or bromination of aromatic sulphonic acids without the use of a solvent and a catalyst.

SUMMARY OF THE INVENTION

It has been found that aromatic sulphonic acids can be chlorinated or brominated without solvents or catalyst if the reaction is carried out in the melt of such an aromatic sulphonic acid.

The invention therefore relates to a process for the preparation of aromatic (di)chlorosulphonic acids and (di)bromosulphonic acids by reacting aromatic sulphonic acids with chlorine or bromine respectively, which process is characterized in that the reaction is carried out in the melt of the aromatic sulphonic acids.

DETAILED DESCRIPTION OF THE INVENTION

For the reaction, chlorine or bromine is passed into the melt of an aromatic sulphonic acid either in elemental form or in the form of a compound which releases elemental chlorine or bromine under the conditions according to the invention. Examples of compounds which may be mentioned which release chlorine or bromine under the conditions according to the invention are sulphuryl chloride or sulphuryl bromide, respectively. In a preferred manner, the process is carried out with elemental chlorine or elemental bromine. In a particularly preferred manner, the process according to the invention relates to the chlorination of aromatic sulphonic acids using elemental chlorine. The elemental chlorine or bromine, or the compound releasing elemental chlorine or bromine, can be passed into the reaction mixture either in the form of a gas or in the liquid state. The elemental halogens are preferably passed in in the form of gas. To carry out the halogenation rapidly by increasing the concentration of the halogen, it can be advantageous to pass in the halogen under increased pressure. For example, the elemental chlorine can thus be passed in either under atmospheric pressure or advantageously at a pressure of between 1 and 6 bar. Depending on the amount of the halogenating agent, the halogenation results in monohalogenated or dihalogenated aromatic sulphonic acids. 90 to 130 mol % of halogenating agent are employed per halogen to be introduced. A dihalogenation can also be carried out in succession in a two-step reaction. In a preferred manner, a monohalogenation is carried out.

The process according to the invention is carried out in the melt of the basic aromatic sulphonic acid. The reaction temperature is therefore above the melting point of this aromatic sulphonic acid. In many cases, the reaction temperature is in the range of from 40°-200° C., preferably in the range of from 50°-120° C. It is preferred to carry out the process in a higher temperature range only in the case of sulphonic acids with high melting points.

According to the invention, it is possible to react aromatic sulphonic acids of the formula

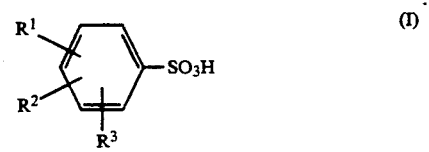

in which $R^1$ denotes hydrogen, straight-chain or branched $C_1$–$C_{20}$-alkyl, $C_3$–$C_8$-cycloalkyl, benzyl, substituted benzyl, phenyl, substituted phenyl, straight-chain or branched $C_1$–$C_{20}$-alkoxy, benzyloxy, substituted benzyloxy, phenoxy, substituted phenoxy, nitro or cyano, $R^2$ represents hydrogen, methyl or ethyl and $R^3$ represents hydrogen, methyl, ethyl, fluorine, chlorine or bromine, where furthermore $R^1$ and $R^2$ together can denote a fused benzene ring or substituted benzene ring, a fused aromatic or non-aromatic 5- or 6-membered heterocycle, or trimethylene or tetramethylene.

Preferably, it is possible to react sulphonic acids of the formula

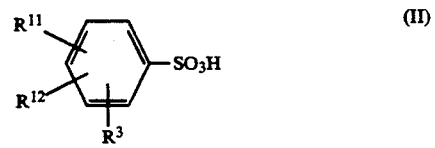

in which $R^{11}$ denotes hydrogen, straight-chain or branched $C_1$–$C_{20}$-alkyl, straight-chain or branched $C_1$–$C_{20}$-alkoxy, cyclopropyl, cyclopentyl, cyclohexyl, benzyl, substituted benzyl, phenyl or substituted phenyl, $R^{12}$ represents hydrogen, methyl or ethyl and $R^3$ has the abovementioned meaning, where furthermore $R^{11}$ and $R^{12}$ together can denote a fused benzene ring or substituted benzene ring, or trimethylene or tetramethylene.

Particularly preferably, it is possible to react sulphonic acids of the formula

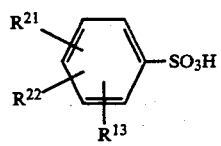

in which
R$^{21}$ denotes hydrogen or straight-chain or branched C$_1$–C$_4$-alkyl and
R$^{22}$ and R$^{13}$ independently of one another represent hydrogen, methyl or ethyl.

In this context, the aromatic sulphonic acid can be employed as such, in many cases also in the form of the sulphonation melt as obtained in the sulphonation of the basic aromatic compound with SO$_3$. In this context, sulphuric acid may be present in an amount of 0.1–25% by weight relative to the total of sulphonic acid and sulphuric acid.

Furthermore, it may be expedient in many cases to carry out the process in the presence of up to 10% by weight of water relative to the sulphonic acid to be reacted. This is true for example when the sulphonic acids are used in the form of their hydrates. Neither the sulphuric acid nor the water are essential for the ability of the process according to the invention to be carried out.

In a furthermore preferred manner, the aromatic sulphonic acid employed is 4-toluenesulphonic acid or a sulphonation melt which mainly contains 4-toluene-sulphonic acid.

Examples of straight-chain or branched C$_1$–C$_{20}$-alkyl are methyl, ethyl, propyl, isopropyl, butyl, isobutyl, tert.-butyl or one of the hexyl, octyl, decyl, dodecyl, hexadecyl or eicosyl isomers. Straight-chain or branched C$_1$–C$_{20}$-alkoxy is derived from the C$_1$–C$_{20}$-alkyl mentioned by uptake of one O atom. C$_1$–C$_{12}$-Alkyl or C$_1$–C$_{12}$-alkoxy is preferred, C$_1$–C$_8$-alkyl or C$_1$–C$_8$-alkoxy is particularly preferred, and C$_1$–C$_4$-alkyl or C$_1$–C$_4$-alkoxy is very particularly preferred.

Substituted benzyl, phenyl, benzyloxy or phenoxy or a substituted fused benzene ring carries a sulphonic acid group or R$^3$.

In the event that R$^1$ and R$^2$ together form a fused 5- or 6-membered heterocycle, this results, together with the benzene ring carrying the radicals R$^1$ and R$^2$, in the series of the benzo-fused aromatic heterocycles or the non-aromatic heterocycles formed by (partial) hydrogenation, with one or two hetero atoms from the group comprising N, O and S, such as indole, indolenine, coumarone, thionaphthene, benzimidazole, benzoxazole, benzothiazole, quinoline, isoquinoline, chromene, chromane and benzoxazine.

In the event that R$^1$ and R$^2$ together form trimethylene or tetramethylene, the result is the indane or tetralin series, respectively.

The chlorine or bromine preferably occupies the position which is favoured according to the general rules of electrophilic aromatic substitution, which are known to those skilled in the art. In the case of 4-sulphotoluene, this is the 2-position. If a sulphonation melt is employed which was formed, for example, by reacting toluene with SO$_3$, this sulphonation melt also contains varying proportions of 2- and 3-toluenesulphonic acid, in addition to 4-toluenesulphonic acid. In such a case, all three isomeric chloro- or bromo-toluenesulphonic acids are formed. They can be isolated in pure form by customary methods of purification or working-up.

EXAMPLE 1

2-Chloro-4-toluene-sulphonic acid from 4-toluenesulphonic acid

Starting from 241.5 g of 4-toluenesulphonic acid hydrate, the water was eliminated using benzene. When water was no longer separated off, the benzene was distilled off. Any remaining benzene was expelled in a stream of nitrogen. 189.9 g (1.10 mol) of 4-toluenesulphonic acid were obtained. Then, chlorine was passed in at 60° C. until the increase in weight of the batch corresponded to the theoretically expected increase (39 g). After remaining chlorine and hydrogen chloride had been expelled in a stream of nitrogen, the effective increase in weight of the batch was 37.4 g (1.06 mol of chlorine). High-performance liquid chromatography analysis (HPLC) showed a content of 88.3% (88.3% of the theoretical yield) of 2-chloro-4-toluenesulphonic acid besides 1.72% (1.72% of the theoretical yield) of 3-chloro-4-toluenesulphonic acid and 1.3% (1.56% of the sulphonic acid employed) of 4-toluenesulphonic acid.

EXAMPLE 2

Chlorination of a Sulphonation Melt

Chlorine was passed at 65° C. into 256.7 g of a sulphonation melt as was obtained in the sulphonation of toluene with sulphur trioxide (contained 72.9% of 4-toluenesulphonic acid and 12.8% of 2-toluenesulphonic acid), until the theoretically expected increase in weight of the batch had been achieved. Remaining chlorine and hydrogen chloride were subsequently expelled with nitrogen. The weight of the batch was now 306.5 g. HPLC analysis showed a content of 62.1% of 2-chloro-4-toluenesulphonic acid, which is 85% of the theoretical yield. 8.1% of 4-chloro-2-toluenesulphonic acid and 3.6% (5% of sulphonic acid employed) of 4-toluenesulphonic acid were also detected.

We claim:
1. A process for the preparation of an aromatic (di)-chlorosulphonic acid or (di)bromosulphonic acid by reacting an aromatic sulphonic acid with a halogenating agent selected from the group consisting of chlorine and bromine, said chlorine and bromine being in elemental form or in the form of a compound which releases chlorine or bromine under the process conditions, wherein the reaction is carried out without the use of a catalyst and in a melt, consisting essentially of the aromatic sulphonic acid at a temperature of 40°–200° C.,
wherein the aromatic sulphonic acid reacted is an aromatic sulphonic acid or mixture of aromatic sulphonic acids of the formula

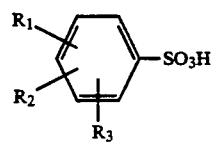

in which
R$_1$ denotes hydrogen, straight-chain or branched C$_1$–C$_{20}$-alkyl, C$_3$–C$_8$-cycloalkyl, benzyl, substituted benzyl, phenyl, substituted phenyl, straight-chain or branched $C_1$–$C_{20}$-alkoxy, benzyloxy, substituted benzyloxy, phenoxy, substituted phenoxy, nitro or cyano, $R_2$ represents hydrogen, methyl or ethyl and $R_3$ represents hydrogen, methyl, ethyl, fluorine, chlorine or bromine, where furthermore $R_1$ and $R_2$ together can denote a fused benzene ring or substituted benzene ring, a fused aromatic or non-aromatic 5- or 6-membered heterocycle, or trimethylene or tetramethylene.

2. The process of claim 1, wherein chlorine or bromine in elemental form is employed.

3. The process of claim 2, wherein elemental chlorine is employed.

4. The process of claim 3, wherein the elemental chlorine is passed in at a pressure of between 1 and 6 bar.

5. The process of claim 1, wherein 90–130 mol % of halogenating agent are employed per halogen to be introduced.

6. The process of claim 1, wherein the reaction is carried out at 50°–120° C.

7. The process of claim 1, wherein the aromatic sulphonic acid reacted is one of the formula

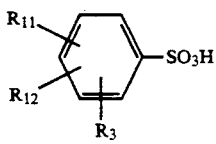

in which $R_{11}$ denotes hydrogen, straight-chain or branched $C_1$–$C_{20}$-alkyl, straight-chain or branched $C_1$–$C_{20}$-alkoxy, cyclopropyl, cyclopentyl, cyclohexyl, benzyl, substituted benzyl, phenyl or substituted phenyl, $R_{12}$ represents hydrogen, methyl or ethyl and $R_3$ has the meaning given in claim 1, where furthermore $R_{11}$ and $R_{12}$ together can denote a fused benzene ring or substituted benzene ring, or trimethylene or tetramethylene.

8. The process of claim 7, wherein the aromatic sulphonic acid reacted is one of the formula

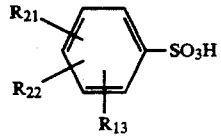

in which $R_{21}$ denotes hydrogen, straight-chain or branched $C_1$–$C_4$-alkyl and $R_{22}$ and $R_{13}$ independently of one another represent hydrogen, methyl or ethyl.

9. The process of claim 1, wherein the aromatic sulphonic acid is employed as sulphonation melt as obtained in the sulphonation of the basic aromatic compound with $SO_3$.

10. The process of claim 7, wherein the aromatic sulphonic acid employed is 4-toluene-sulphonic acid.

* * * * *